United States Patent
Karim et al.

(10) Patent No.: US 6,989,347 B2
(45) Date of Patent: *Jan. 24, 2006

(54) CATALYSTS FOR THE OXIDATION OF UNSATURATED ALDEHYDES TO PRODUCE CARBOXYLIC ACIDS AND METHODS OF MAKING THE SAME

(75) Inventors: Khalid Karim, Manchester (GB); Yajnavalkya Subrai Bhat, Riyadh (SA); Syed Irshad Zaheer, Riyadh (SA); Asad Ahmad Khan, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 186 days.

This patent is subject to a terminal disclaimer.

(21) Appl. No.: 10/133,549

(22) Filed: Apr. 25, 2002

(65) Prior Publication Data

US 2002/0115887 A1   Aug. 22, 2002

Related U.S. Application Data

(62) Division of application No. 09/560,988, filed on Apr. 28, 2000, now Pat. No. 6,444,845.

(51) Int. Cl.
*B01J 23/00* (2006.01)
*B01J 27/19* (2006.01)
*B01J 21/08* (2006.01)
*B01J 21/12* (2006.01)
*B01J 21/14* (2006.01)

(52) U.S. Cl. .................... 502/311; 502/211; 502/248; 502/255; 502/306; 502/308; 502/312; 502/317; 502/321; 502/322; 502/323; 502/415; 502/439; 502/104; 502/110; 502/113; 502/117

(58) Field of Classification Search ............... 502/248, 502/255, 211, 306, 308, 311, 312, 317, 321–323, 502/415, 439, 104, 110, 113, 117
See application file for complete search history.

(56) References Cited

U.S. PATENT DOCUMENTS

| | | | | |
|---|---|---|---|---|
| 4,075,283 A | * | 2/1978 | Shiraishi et al. | 423/239 |
| 4,289,654 A | | 9/1981 | Bertolini | |
| 4,524,236 A | * | 6/1985 | McCain | 585/658 |
| 4,568,790 A | * | 2/1986 | McCain | 585/658 |
| 4,596,787 A | * | 6/1986 | Manyik et al. | 502/312 |
| 4,946,819 A | * | 8/1990 | Sasaki et al. | 502/214 |
| 5,162,578 A | * | 11/1992 | McCain, Jr. et al. | 562/512.2 |
| 5,324,695 A | * | 6/1994 | Karrer et al. | 502/27 |
| 5,422,328 A | * | 6/1995 | Ushikubo et al. | 502/312 |
| 5,472,925 A | * | 12/1995 | Ushikubo et al. | 502/312 |
| 5,807,531 A | | 9/1998 | Hibst | |
| 5,907,056 A | * | 5/1999 | Karim et al. | 562/549 |
| 5,959,143 A | | 9/1999 | Sugi | |
| 6,028,221 A | * | 2/2000 | Karim et al. | 562/548 |
| 6,030,920 A | * | 2/2000 | Karim et al. | 502/312 |
| 6,043,186 A | * | 3/2000 | Komada et al. | 502/312 |
| 6,060,421 A | * | 5/2000 | Karim et al. | 502/303 |
| 6,063,728 A | * | 5/2000 | Hinago et al. | 502/300 |
| 6,084,126 A | | 7/2000 | Hibst | |
| 6,087,297 A | * | 7/2000 | Karim et al. | 502/303 |
| 6,143,690 A | * | 11/2000 | Komada et al. | 502/211 |
| 6,184,173 B1 | | 2/2001 | Hibst | |
| 6,239,325 B1 | * | 5/2001 | Kishimoto et al. | 585/658 |
| 6,310,241 B1 | * | 10/2001 | Karim et al. | 562/549 |
| 6,428,765 B1 | * | 8/2002 | Bedard et al. | 423/593 |
| 6,518,216 B1 | * | 2/2003 | Han et al. | 502/215 |
| 6,531,631 B1 | * | 3/2003 | Karim et al. | 562/549 |
| 6,638,891 B2 | * | 10/2003 | Karim et al. | 502/302 |

FOREIGN PATENT DOCUMENTS

| | | |
|---|---|---|
| DE | 19821056 A | 8/1999 |
| DE | 19815281 | 10/1999 |
| EP | 293859 | 12/1988 |
| EP | 427508 | 5/1991 |
| EP | 685259 | 12/1995 |
| EP | 711745 | 5/1996 |
| EP | 774297 | 5/1997 |
| JP | 4321642 | 11/1992 |
| JP | 5317713 | 12/1993 |
| JP | 5329371 | 12/1993 |
| JP | 11343261 | 12/1999 |

OTHER PUBLICATIONS

International Search Report in PCT Appl. No. PCT/EP 01/04433 dated Jan. 25, 2002.

* cited by examiner

*Primary Examiner*—Cam N. Nguyen
(74) *Attorney, Agent, or Firm*—Kramer Levin Naftalis & Frankel LLP

(57) ABSTRACT

A catalyst composition for the production of carboxylic acids by the oxidation of the corresponding unsaturated aldehydes, and methods for making and using the catalyst compositions. The catalysts include compositions of the formula:

$$Mo_a V_b Al_c X_d Y_e O_z$$

wherein X is at least one element selected from W and Mn; Y is at least one element selected from Pd, Sb, Ca, P, Ga, Ge, Si, Mg, Nb, and K; a is 1; b is 0.01–0.9; c is 0<0.2; d is 0<0.5; e is 0<0.5; and z is an integer representing the number of oxygen atoms required to satisfy the valency of the remaining elements in the composition. Using the catalyst composition of the present invention, one may effectively oxidize the desired starting materials at relatively high levels of conversion, selectivity, and productivity, and with minimal side products.

13 Claims, No Drawings

CATALYSTS FOR THE OXIDATION OF UNSATURATED ALDEHYDES TO PRODUCE CARBOXYLIC ACIDS AND METHODS OF MAKING THE SAME

This is a Divisional of application Ser. No. 09/560,988, filed Apr. 28, 2000 now U.S. Pat. No. 6,444,845 B1.

BACKGROUND OF THE INVENTION

1. Field of the Invention

The present invention relates to new catalysts for the oxidation of unsaturated aldehydes to produce carboxylic acids and to methods of making and using such catalysts. More particularly, this invention relates to mixed metal oxide catalysts for the oxidation of unsaturated aldehydes, such as acrolein, to produce the corresponding alpha-beta unsaturated carboxylic acids, i.e., acrylic acid.

2. Description of the Prior Art

Several publications are referenced in this application. These references describe the state of the art to which this invention pertains, and are incorporated herein by reference.

The vapor phase oxidation of acrolein for the production of acrylic acid is known in the art. Various references disclose the use of mixed metal oxide catalysts containing molybdenum and vanadium, alone or in combination with other metals, for use in the catalytic oxidation of acrolein. The following is a brief summary of the disclosures of several of these references.

Japanese Patent Publication No. 11343261 discloses the preparation of acrylic acid by catalytic oxidation of acrolein in the presence of a metal oxide catalyst. The catalyst has the formula $MoV_iSb_jA_k$, wherein A is Nb or Ta, i and j are 0.01–1.5, the ratio of j to i is 0.3–1.0, and k is 0.001–3.0. Acrolein is oxidized in the presence of oxygen and the metal catalyst at 260° C. and a contact time of 0.95 seconds, wherein the ratio of Mo:V:Sb:Nb is 1:0.3:0.23:0.08. A 97.2% yield of acrylic acid is achieved.

German Patent Publication No. 19815281 describes the preparation of molybdenum and/or vanadium containing mixed metal oxide catalysts for the partial oxidation of acrolein to acrylic acid. The mixed metal oxide catalysts have the formula $A_pB_qC_r$, wherein A is $Mo_{12}V_aX^1_bX^2_cX^3_dX^4_eX^5_fX^6_gO_x$, B is $X^7Cu_hH_iO_y$, C is $X^8Sb_jH_kO_z$, $X^1$ is W, Nb, Ta, Cr, and/or Ce, $X^2$ is Cu, Ni, Co, Fe, Mn, and/or Zn, $X^3$ is Sb and/or Bi, $X^4$ is Li, Na, K, Rb, Cs and/or H, $X^5$ is Mg, Ca, Sr, and/or Ba, $X^6$ is Si, Al, Ti, and/or Zr, $X^7$ is Mo, W, V, Nb, and/or Ta, $X^8$ is Cu, Ni, Zn, Co, Fe, Cd, Mn, Mg, Ca, Sr, and/or Ba, a is 1–8, b is 0.2–5, c is 0–23, d is 0–50, e is 0–2, f is 0–5, g is 0–50, h is 0.3–2.5, i is 0–2, j is 0.05–50, k is 0–50, the values of x, y, and z depend on the valence and relative abundance of the remaining elements in the composition, and p, q, and r are greater than or equal to zero, with the proviso that p/(q+r) is 1–20. The mixed oxide catalysts are prepared from finely ground precursor components which are mixed, dried, and calcined at 250–500° C.

European Patent Publication Nos. 774297, 711745, 0685259, 427508, and 293859 relate to the use of mixed metal oxide catalysts containing molybdenum and vanadium in the gas phase oxidation of acrolein. WO 9627437 discloses the manufacture of a highly active catalyst having high mechanical strength suitable for the gas phase oxidation of acrolein. The catalyst contains molybdenum, vanadium, copper, and antimony as essential components. Similarly, U.S. Pat. No. 4,289,654 describes the use of a mixed metal oxide catalyst containing molybdenum, vanadium, tungsten, copper, and chromium on an alpha alumina support to oxidize acrolein to acrylic acid at 97% selectivity.

Japanese Patent Publication Nos. 05329371 and 05317713 relate to the production of a highly selective catalyst for acrolein oxidation. The catalyst is produced from a catalyst precursor containing molybdenum and vanadium, among other components. Japanese Patent Publication No. 04321642 describes the use of a molybdenum and vanadium based metal oxide catalyst to oxidize acrolein in the gas phase. The catalyst has the formula $Mo_aV_bSi_cNa_dA_eX_fY_gO_h$, wherein A is Fe, Cr, Co, and/or Sr, X is Ge, Se, Sn, Te, and/or Sm, Y is Mg, Ti, Cu, Zn, Nb, Mn, Ni, Ag, Ta, Bi, Ce, and/or W, and a, b, c, d, e, f, and g are integers, such that the ratio of one to the other is a:b:c:d:e:f:g or 12:(1–6):(0.1–15):(0–2):(0.1–3):(0.1–3):(0–3),and h is an integer which satisfies the valance of the remaining elements of the composition. The patent describes the use of such a catalyst (having a formula $Mo_{12}V_3Si_4FeGe_{0.2}O_h$) with a gas mixture of 5% acrolein, 10% oxygen, 30% steam, and 55% nitrogen at 270° C. to yield acrylic acid with 95% selectivity and at 99% conversion of acrolein.

Soviet Union Patent Publication Nos. 858916 and 899112 describe a catalyst containing vanadium oxide and molybdenum oxide, and copper oxide as a promoter on a silica support suitable for acrolein oxidation to acrylic acid. The catalyst exhibits increased activity and mechanical strength due, at least in part, to its method of manufacture. The catalyst is prepared by granulating the catalyst material after drying and adding promoter and a binder compound during granulation. Great Britain Patent Publication No. 1586173 discloses the use of metal oxide catalysts containing molybdenum, vanadium, chromium, copper, and a metal selected from Mb, Ta, and/or Ti, for the oxidation of acrolein to acrylic acid with improved conversion and selectivity. The ratio of molybdenum, vanadium, chromium, copper, and the metal is Mo:V:Cr:Cu:M or 15:(5–7):(0.7–0.8):(2.4–2.8):(1.5–2). A feedstock containing 5.6 mol % acrolein, 30 mol % nitrogen, and oxygen was passed through the catalyst and heated to 300° C. in a 3.05 m×2.54 cm stainless steel pipe reactor. At a contact time of 2.9 seconds, 99% of the acrolein was converted to acrylic acid at a selectivity for acrylic acid and carbon oxides of 93.4% and 4.4%, respectively.

The catalysts described above exhibit decreased stability over time (see European Patent Publication No. 0711745, Japanese Patent Publication No. 25914, and *Cat. Rev. Sci. Eng.*, vol. 35, p. 213 (1993)). This is due to the generation of $V_2O_5$, which is responsible for the slow decay of the catalyst performance. Therefore, it would be desirable to develop a molybdenum and vanadium based catalyst for the production of carboxylic acids from aldehydes which would exhibit enhanced performance and stability.

SUMMARY OF THE INVENTION

The present invention provides a new highly selective catalyst system for the oxidation of aldehydes in the gas phase. The catalyst compositions of the present invention are particularly well suited for the catalytic preparation of alpha-beta unsaturated carboxylic acids from the corresponding aldehydes, e.g., the production of acrylic acid from acrolein. Using the improved catalyst, acrolein is oxidized in the presence of molecular oxygen at relatively high levels of conversion, selectivity, and productivity, at temperatures preferably from about 150° C. to about 450° C.

The catalyst compositions of the present invention include compositions of the formula:

wherein:
X is at least one element selected from W and Mn;
Y is at least one element selected from Pd, Sb, Ca, P, Ga, Ge, Si, Mg, Nb, and K;
a is 1;
b is 0.01–0.9;
c is 0<0.2;
d is 0<0.5;
e is 0<0.5; and
z is an integer representing the number of oxygen atoms required to satisfy the valency of Mo, V, Al, X, and Y in the composition. The catalysts are preferably produced using the methods disclosed herein.

DETAILED DESCRIPTION OF THE PREFERRED EMBODIMENTS

One aspect of the invention relates to a catalyst for the production of olefins from hydrocarbons via oxidative dehydrogenation. The catalyst composition comprises a compound of the formula:

wherein:
X is at least one element selected from W and Mn;
Y is at least one element selected from Pd, Sb, Ca, P, Ga, Ge, Si, Mg, Nb, and K;
a is 1;
b is 0.01–0.9;
c is 0<0.2;
d is 0<0.5;
e is 0<0.5; and
z is an integer representing the number of oxygen atoms required to satisfy the valency of the remaining elements in the composition.

The catalyst composition of the present invention can be used with or without a support. The choice of the components of the composition used, as well as the specific procedures used to prepare the catalyst composition, can have a significant effect on its performance. The components of the catalyst composition are in combination with oxygen as oxides.

Preferably, the catalyst compositions are prepared from a solution of soluble compounds (salts, complexes or other compounds) of each of the metals. The solution is preferably an aqueous system having a pH of 1 to 10, and more preferably a pH of 1 to 7, preferably at a temperature from about 30° C. to about 100° C. Water is removed, e.g., by filtration, to complete dryness. The catalyst is dried in an oven at a temperature, e.g., from 100° C. to 130° C. The dried catalyst is calcined by heating to a temperature from about 250° C. to about 600° C., preferably about 250° C. to about 450° C., in air or oxygen for about one hour to about 16 hours to produce the desired catalyst composition.

Suitable supports for the catalyst include alumina, silica, titania, zirconia, zeolites, silicon carbide, molybdenum carbide, molecular sieves and other microporous/nonporous materials, and mixtures thereof Support materials can be pretreated with acids, such as HCl, HNO$_3$, H$_2$SO$_4$, per acids or heteropoly acids, and alkali base materials such as KOH or NaOH. When used on a support, the support usually comprises from about 5% to about 95% by weight, preferably from about 50 to 90% by weight of the catalyst composition, with from about 5% to about 50% or the remainder being the catalyst.

Preferably, molybdenum is introduced into the solution in the form of ammonium salts, such as ammonium paramolybdate, or organic acid salts of molybdenum, such as acetates, oxalates mandelates, and glycolates. Some other partially water soluble molybdenum compounds which may be used include molybdenum oxides, molybdic acid, and chlorides of molybdenum.

Preferably, vanadium, aluminum, gallium, silicon, germanium, antimony, phosphorus, niobium, potassium, magnesium, palladium, tungsten, and manganese are introduced into the catalyst slurry in the form of salts or acids, oxides, hydrates, acetates, chlorides, nitrate acetates, oxalates, and tartrates.

The catalysts of the present invention are preferably used in the oxidation of alpha-beta unsaturated aldehydes to the corresponding carboxylic acids. In a preferred embodiment, the feed mixture contains lower alkyl (preferably 2–6 carbon atoms, more preferably 2–6 carbon atoms) branched or straight chained unsaturated aldehydes. However, the method of the present invention may also be used for the oxidation of lower alkyl (preferably 2–6 carbon atoms, more preferably 3–6 carbon atoms) branched or straight chained alkanes or alkenes to the corresponding carboxylic acids, as well as for the ammoxidation of lower alkyl (preferably 2–6 carbon atoms, more preferably 3–6 carbon atoms) branched or straight chained alkanes or alkenes, such as methacrolein to methacrylic acid. In addition, feed comprising acrolein obtained by direct oxidation of propylene or propane containing by-products of carbon oxides, acrylic acid, acetic acid, acetone and acetaldehyde can also be used for such a reaction. These by-products are not harmful to the catalysts disclosed in the present invention.

The reaction mixture in the method is generally a gaseous mixture of 0.1 to 99 mol % unsaturated aldehydes, such as acrolein, 0.1 to 99 mol % molecular oxygen either as pure oxygen or in the form of air, zero to 50 mol % water in the form of steam, and 0 to 90 mol % nitrogen or another inert gas. The gaseous mixture is generally introduced into a reaction zone having a temperature of about 150° C. to about 400° C. or 450° C., and preferably 170° C. to 350° C., more preferably 200° C. to 300° C. The reaction zone generally has a pressure of 15 to 400 psi or 1 to 50 bar, and preferably 1 to 30 bar, the contact time between the reaction mixture and the catalyst is about 0.01 second to 100 seconds, and preferably 0.1 second to 10 seconds, and the space hourly velocity is about 50 to about 50,000 h$^{-1}$, and preferably about 500 to about 20,000 h$^{-1}$ and more preferably from 100 to 10,000 h$^{-1}$. The process is generally carried out in a single stage fixed bed or fluidized bed reactor, or solid moving bed reactor wherein all the oxygen and reactants are supplied as a single feed, with non-reacted starting materials being recycled. However, multiple stage addition of oxygen to the reactor with intermediate hydrocarbon feed can be used. This may improve productivity and avoid potentially hazardous conditions such as hydrocarbon and oxidant explosive mixture or mixture of hydrocarbon and oxidant in explosive envelope, generation of hot spots which ultimately affect the product distribution and catalyst life.

In one embodiment, the feed comprises a mixed gas containing about one to about 25% by volume alpha beta unsaturated aldehyde, about 0.25 to about 30% by volume oxygen, zero to about 50% by volume steam and about 10 to about 80% by volume inert gas and the process provides an alpha beta unsaturated aldehyde conversion of at least 98% with a selectivity to corresponding unsaturated carboxylic acid of at least 80%.

The following examples are intended to be illustrative of this invention. They are, of course, not to be taken to in any way limit the scope of this invention. Numerous changes and modifications can be made with respect to the invention without departing from the spirit or scope of the present invention.

EXAMPLES

Example 1

$$Mo_1V_{0.396}Al_{2.04e-1}Mn_{8.96e-2}Sb_{2.51e-2}Ca_{6.89e-3}$$

Ammonium metavanadate (Aldrich Chemicals, Assay=99.0%), 5.7 grams, was added to distilled water and heated to 90° C. with stirring. A yellow colored solution with pH between 4 and 7 was obtained (Solution A). Antimony trioxide, 0.45 grams, and 11 grams of oxalic acid were added with water to the solution with continuous stirring, followed by the addition of the required amount of calcium, aluminum, and manganese salts solution slowly to the mixture. Ammonium paramolybdate tetrahydrate (Aldrich Chemicals A.C.S. -12054-75-2), 21.7 grams, was added to the solution. This mixture was then dried. The resulting solid was dried in an oven at 100–120° C. The dried material was cooled to room temperature and calcined at 300 to 600° C. Calcined catalyst was formulated into uniform particles of 40–60 mesh size and loaded in a stainless steel fixed bed tubular autoclave reactor. The catalyst was tested with a gas feed composition of nitrogen: oxygen: acrolein: carbon oxides: water in the ratio of 19.2:1.24:1.0:0.43:4.80 at 235° C., at a pressure of 15 psi and a total flow of 115 cc/min. Reaction product showed a 100% conversion of acrolein with 85% selectivity for acrylic acid and 15% for carbon oxide products. A space time yield of 176 g of acrylic acid per liter of catalyst per hour was achieved under present process conditions.

Example 2

$$Mo_1V_{0.398}Al_{2.04e-4}Mn_{1.0e-4}Nb_{1.25e-1}$$

Ammonium metavanadate (Aldrich Chemicals, Assay=99.0%), 7.6 grams, was added to distilled water and heated to 90° C. with stirring. A yellow colored solution with pH between 4 and 7 was obtained (Solution A). Antimony trioxide, 0.45 grams, and 28.0 grams of oxalic acid were added with water to the solution with continuous stirring, followed by the addition of the required amount of aluminum, manganese and niobium salt solution slowly to the mixture. Ammonium paramolybdate tetrahydrate (Aldrich Chemicals A.C.S. -12054-85-2), 21.7 grams, was added to the solution. This mixture was then dried. The resulting solid was dried in an oven at 100–120° C. The dried material was cooled to room temperature and calcined at 300 to 600° C. Calcined catalyst was formulated into uniform particles of 40–60 mesh size and loaded in a stainless steel fixed bed tubular autoclave's reactor. The catalyst was tested with a gas feed composition of nitrogen: oxygen: acrolein: carbon oxides: water in the ratio of 19.2:1.24:1.0:0.43:4.80 at 235° C., at a pressure of 15 psi and a total flow of 115 cc/min. Reaction product showed a 100% conversion of acrolein with a 80.8% selectivity to acrylic acid and 16% to carbon oxides products. A space time yield of 167 g of acrylic acid per liter of catalyst per hour was achieved under present process conditions.

The catalyst compositions disclosed in the invention showed an optimum redox and oxygenation function which are believed to derive from acid activity. The catalysts exhibited superior performance which may be attributed to the composition of the metal oxides controlling the activity of the catalyst and the selectivity for the oxygenated products. Because of the high activity, a process using the catalyst can be run at temperatures which are relatively lower than the temperatures described in the prior art. The higher temperatures required in the prior art have a significant impact on catalyst life. Furthermore, the catalysts disclosed in the present invention did not show any deactivation until after six months on stream.

The above description of the invention is intended to be illustrative and not limiting. Various changes or modifications in the embodiments described may occur to those skilled in the art. These can be made without departing from the spirit or scope of the invention.

We claim:

1. A catalyst for oxidation of unsaturated aldehydes to carboxylic acids, said catalyst comprising a catalyst composition having the formula:

$$Mo_aV_bAl_cMn_dY_eO_z$$

wherein:
Y is at least one element selected from the group consisting of Pd, Sb, Ca, P, Ga, Ge, Si, Mg, Nb, and K;
a is 1;
b is 0.01 to 0.9;
c is >0 to 0.2;
d is >0 to 0.5;
e is >0 to 0.5; and
z is the number of oxygen atoms required to satisfy the valency of Mo, V, Al, Mn, and Y in said composition.

2. The catalyst of claim 1, further comprising a support.

3. The catalyst of claim 2, wherein said support is selected from the group consisting of alumina, silica, titania, zirconia, zeolites, silicon carbide, molecular sieves, microporous or nonporous materials, and mixtures thereof.

4. The catalyst of claim 2, wherein the support is pretreated with acid or base materials.

5. The catalyst of claim 2, wherein the catalyst composition comprises from about 5 to about 50% by weight of the catalyst and the support comprises from about 50% to about 95% by weight of the catalyst.

6. The catalyst of claim 1, wherein the catalyst composition is a calcined composition formed at about 300° C. to about 600° C.

7. A method for making a catalyst composition comprising forming a mixture containing compounds of Mo, V, Al, Mn, and Y in an aqueous solution at a pH from about 1 to about 10; drying said mixture to form dried solid material; calcining said dried solid material at a temperature from about 250° C. to about 450° C. to form the catalyst composition;

wherein the compounds of Mo, V, Al, Mn and Y are sufficient to provide a catalyst composition having the formula:

$$Mo_aV_bAl_cMn_dY_eO_z$$

wherein:
Y is at least one element selected from the group consisting of Pd, Sb, Ca, P, Ga, Ge, Si, Mg, Nb, and K;
a is 1;

b is 0.01 to 0.9;
c is >0 to 0.2;
d is >0 to 0.5;
e is >0 to 0.5; and
z is the number of oxygen atoms required to satisfy the valency of Mo, V, Al, Mn, and Y in said composition.

8. The method of claim 7, wherein Y comprises Sb.

9. The method of claim 8, wherein said catalyst composition is a calcined composition formed at about 300° C. to about 600° C.

10. The method of claim 7, wherein Y comprises Sb and Ca.

11. The method of claim 7, wherein Y consists essentially of Sb and Ca.

12. The method of claim 7, wherein said mixture of Mo, V, Al, Mn and Y is formed at a pH from about 1 to about 7.

13. The method of claim 12, wherein Y consists essentially of Sb and Ca.

* * * * *